US010226391B2

(12) United States Patent
Ikoro

(10) Patent No.: US 10,226,391 B2
(45) Date of Patent: Mar. 12, 2019

(54) DEVICES AND METHODS FOR BODY PROTECTION AGAINST MOISTURE AND CONTAMINANTS

(71) Applicant: Oby C. Ikoro, Stoughton, MA (US)

(72) Inventor: Oby C. Ikoro, Stoughton, MA (US)

( * ) Notice: Subject to any disclaimer, the term of this patent is extended or adjusted under 35 U.S.C. 154(b) by 199 days.

(21) Appl. No.: 15/151,481

(22) Filed: May 10, 2016

(65) Prior Publication Data
US 2016/0324699 A1   Nov. 10, 2016

Related U.S. Application Data

(60) Provisional application No. 62/159,304, filed on May 10, 2015.

(51) Int. Cl.
*A61F 15/00* (2006.01)
*A61F 13/00* (2006.01)
*A61F 13/02* (2006.01)

(52) U.S. Cl.
CPC .......... *A61F 15/008* (2013.01); *A61F 13/025* (2013.01); *A61F 13/0233* (2013.01); *A61F 2013/004* (2013.01); *A61F 2013/00165* (2013.01); *A61F 2013/00182* (2013.01); *A61F 2013/00268* (2013.01)

(58) Field of Classification Search
CPC .... A61F 15/008; A61F 15/04; A61F 13/0233; A61F 13/025; A61F 2013/00165; A61F 2013/00182; A61F 2013/00268; A61F 2013/004
See application file for complete search history.

(56) References Cited

U.S. PATENT DOCUMENTS

| 3,741,203 | A * | 6/1973 | Liman | A61F 15/004 602/3 |
| 5,016,648 | A * | 5/1991 | Brown | A61F 13/041 128/846 |
| 5,407,419 | A * | 4/1995 | Kelly | A61F 13/041 383/71 |
| 5,592,953 | A * | 1/1997 | Delao | A61F 15/004 128/882 |
| 6,210,352 | B1 * | 4/2001 | Williams | A61F 15/004 128/849 |
| 6,225,523 | B1 * | 5/2001 | Masini | A61F 13/00038 602/58 |
| 6,276,364 | B1 * | 8/2001 | Warner | A61F 15/004 128/846 |
| 2002/0007135 | A1 * | 1/2002 | Thomas, III | A61F 15/004 602/41 |
| 2004/0199974 | A1 * | 10/2004 | Fancher | A61F 13/06 2/59 |
| 2009/0221945 | A1 * | 9/2009 | Andersson | A61F 13/041 602/3 |
| 2011/0082434 | A1 * | 4/2011 | Sager | A61F 15/004 604/385.01 |
| 2011/0087144 | A1 * | 4/2011 | Lee | A61F 13/041 602/3 |

(Continued)

*Primary Examiner* — Kristen Matter
(74) *Attorney, Agent, or Firm* — Joseph Stecewycz

(57) ABSTRACT

A nonpermeable enclosure formed from a clear, waterproof fabric, has a cover ridge for insertion into a channel so as to produce a barrier against moisture and contaminants, and is attached to a closure band for securing the nonpermeable enclosure over a wearer's hand.

16 Claims, 12 Drawing Sheets

(56) References Cited

U.S. PATENT DOCUMENTS

| | | | |
|---|---|---|---|
| 2011/0245744 A1* | 10/2011 | Bellamy | A61F 13/10 602/3 |
| 2012/0144547 A1* | 6/2012 | Collins | A41D 13/1236 2/67 |
| 2013/0212774 A1* | 8/2013 | Tuttle | A41D 19/015 2/160 |
| 2015/0119774 A1* | 4/2015 | Rogers | A61F 13/00068 602/3 |
| 2016/0038354 A1* | 2/2016 | Myers | A61F 15/004 602/3 |
| 2016/0136000 A1* | 5/2016 | Gaffney | A61F 15/004 602/3 |

\* cited by examiner

DEVICES AND METHODS FOR BODY PROTECTION AGAINST MOISTURE AND CONTAMINANTS

CROSS REFERENCE TO RELATED APPLICATION

The present Application is related to Provisional Patent Application entitled "Water Proof Device for Body," filed 10 May 2015 and assigned filing No. 62/159,304, incorporated herein by reference in its entirety.

FIELD OF THE INVENTION

The present invention relates to devices and methods for protection of body areas against ambient moisture and contaminants and, in particular, for protection of body wounds from water and contamination.

BACKGROUND OF THE INVENTION

It is known in the art that care givers experience difficulty in attending to patients who have sensitive areas on their skin, or wounds that need to be kept dry. Attempting to bathe such individuals, for example, becomes challenging and difficult as certain areas of the patient's body need to be kept dry, or free from contaminants, while attempting to complete the bathing routine.

Merely covering the problem area on a patient using a conventional bandage is not acceptable, as such methods cannot guarantee that water leakage or other contamination does not occur.

What is needed is a method of protecting or sealing off part of a person's body so that the person can shower, bathe, or immerse into water or a fluid mixture, while protecting a wound or sensitive area from the water or fluid.

BRIEF SUMMARY OF THE INVENTION

In one aspect of the present invention, a protective device suitable for keeping moisture from a selected region of a body, the protective device comprising: a closure band formed from a flexible substrate, the closure band having a first channel imbedded in a first substrate surface and a first ridge disposed on a second substrate surface in a raised configuration, the closure band further having an adhesive strip on the second substrate surface for attaching the closure band to the body proximate the selected region; and a nonpermeable enclosure formed from a clear, waterproof fabric, the nonpermeable enclosure having a first cover ridge disposed on a surface of the nonpermeable enclosure in a raised configuration, the first cover ridge inserted into the first channel so as to produce a barrier against moisture and contaminants between the closure band and the nonpermeable enclosure.

In another aspect of the present invention, a protective device suitable for keeping moisture from a selected region of a body comprises: a closure band formed from a flexible plastic substrate, the closure band having a first channel and a second channel imbedded in a first substrate surface and a first ridge and a second ridge disposed on a second substrate surface in a raised configuration, the closure band further having a pair of adhesive strips on the second substrate surface for attaching the closure band to the body proximate the selected region; and a nonpermeable enclosure formed from a clear, hypoallergenic material, the protective covering having a first cover ridge and a second cover ridge disposed on a surface of the protective covering in a raised configuration, the first cover ridge inserted into the first channel so as to produce a barrier against moisture and contaminants between the closure band and the protective covering, and the second cover ridge inserted into the second channel so as to produce a second barrier.

In still another aspect of the present invention, a method for keeping moisture from a selected region of a body comprises the steps of: providing a closure band formed from a flexible substrate, the closure band having a channel imbedded in a first substrate surface and a ridge disposed on a second substrate surface in a raised configuration, the channel extending into the ridge, the closure band further having an adhesive strip on the second substrate surface; attaching the closure band to the selected region of the body using the adhesive strip; providing a nonpermeable enclosure configured to cover the selected region of the body, the nonpermeable enclosure having a cover ridge configured for releasable attachment to the channel; and inserting the cover ridge into the channel so as to produce a barrier against moisture and contaminants.

The additional features and advantage of the disclosed invention is set forth in the detailed description which follows, and will be apparent to those skilled in the art from the description or recognized by practicing the invention as described, together with the claims and appended drawings.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures, in which.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

The present invention relates generally to a method and device for protecting selected areas of the body from moisture, water, or other contaminants. Basically, the device comprises a band or cuff with surface channels and ridges, and a nonpermeable protective covering. The protective covering can be adapted for placement over a hand, over a forearm, or over an expanse of a body such as the chest area. The band has one or more adhesive strips on one side for attachment to the wrist, the forearm, or the chest, for example. The protective covering may have a single opening, for covering the hand, or two openings for placement over the forearm, or may be a shallow pouch. Ridges in the protective covering serve to releasable attach the protective covering to the band or cuff. This two piece configuration allows for reuse of the band or cuff. In an alternative embodiment, the band may be fabricated integral with the protective covering to provide a single-piece unit.

Figure 1:
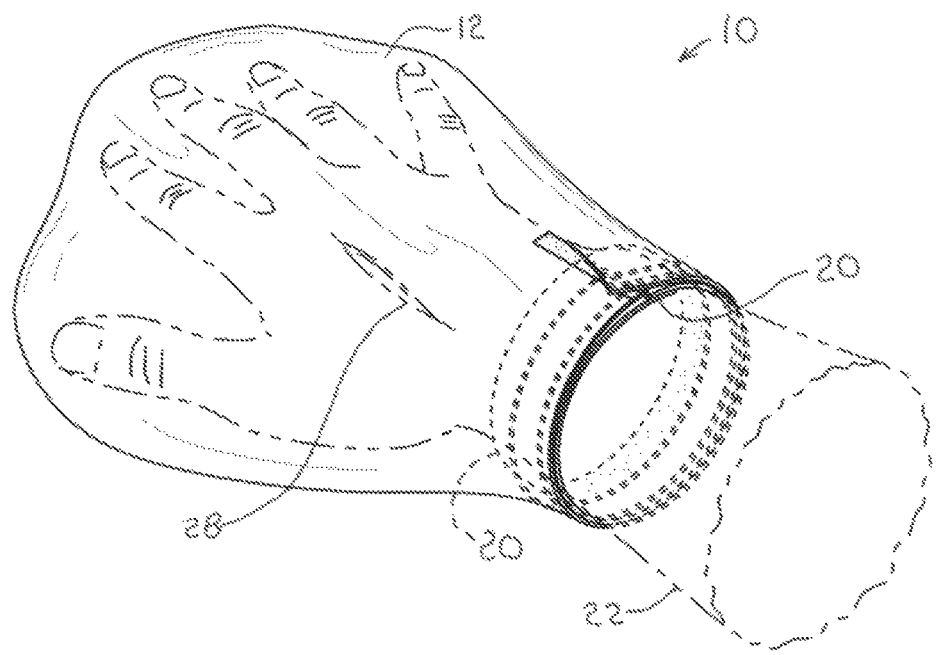
FIG. 1 is a diagrammatical illustration of a protective covering comprising a nonpermeable enclosure and a closure band placed onto a user's hand, in accordance with the present invention.

There is shown in FIG. 1 a single opening protective covering 10 comprising a nonpermeable enclosure 12 and a closure band 20, in accordance with the present invention. In the particular embodiment shown, the protective covering 10 has been sized and shaped to fit over a selected region of a user's body, such as the user's hand 22 as shown, so as to prevent moisture or particulate matter from contacting a wound 28 or other injury on the user's hand 22. The closure band 20 is: (i) first attached to the user's hand 22, and (ii) the nonpermeable enclosure 12 is releasably fastened to the closure band 20 by which the nonpermeable enclosure 12 is secured onto the user's hand 22.

Figure 2:
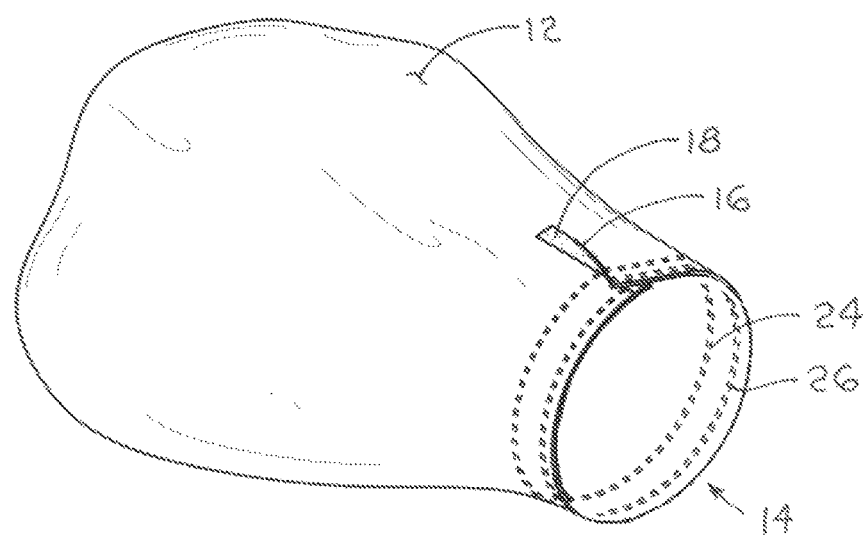
FIG. 2 is a diagrammatical view of the nonpermeable enclosure of FIG. 1.

The nonpermeable enclosure 12 functions to keep out moisture, water, and contaminants, and may accordingly be fabricated from a hypoallergenic material, such as a flexible plastic, a coated fabric, or other suitable flexible material, for example. As shown in FIG. 2, an adjustment slit 16 may be provided in the nonpermeable enclosure 12 to enable the user to close the opening 14 after the hand 22 has been inserted, and the nonpermeable enclosure 12 is secured onto the closure band 20. In an alternative embodiment, the closure band 20 and the nonpermeable enclosure 12 may be formed as a single unitary component (not shown) by which the closure band 20 is secured about the user's hand 22 after the user's hand 22 has been placed into the nonpermeable enclosure 12.

Figure 3:
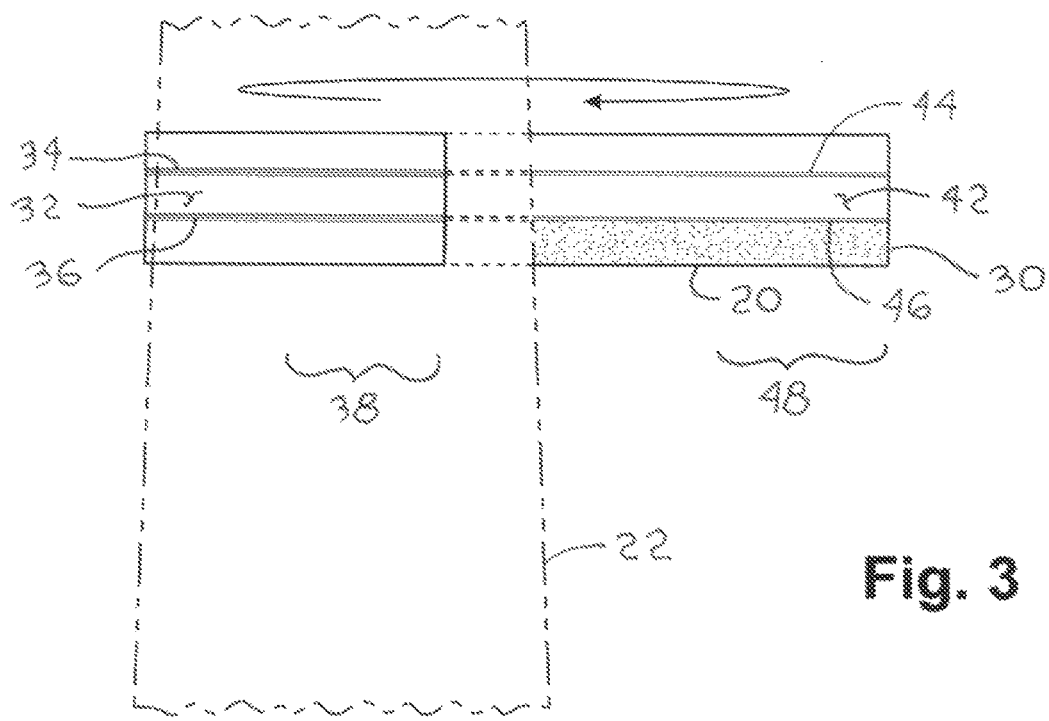
FIG. 3 is a diagrammatical illustration of the placement of the closure band of FIG. 1 onto the user's hand.
Figure 4:
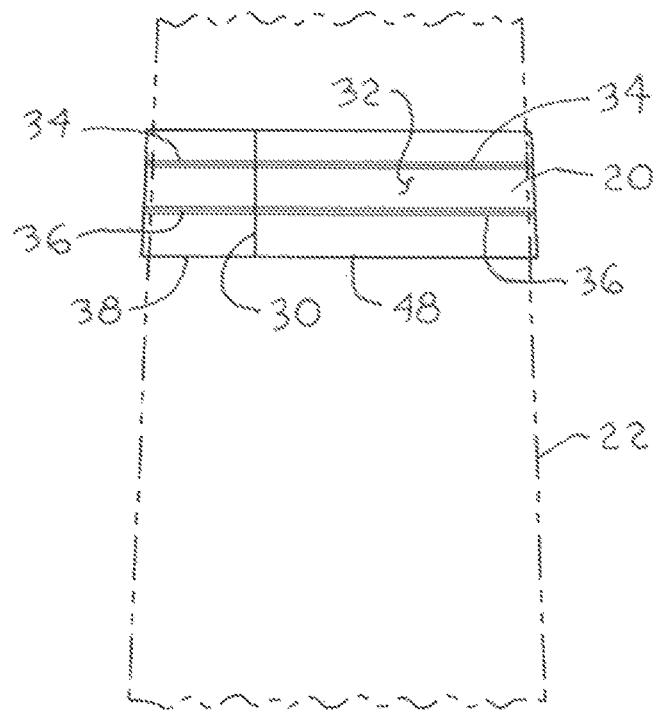
FIG. 4 is a diagrammatical illustration of the placement of the closure band of FIG. 1 onto the user's hand.

FIG. 3 shows the closure band 20 in the process of being secured about the user's hand 22, as indicated by the arrow. For clarity of illustration, the nonpermeable enclosure 12 is not shown. In an exemplary embodiment, the closure band 20 is formed from a flexible substrate, such as a plastic material, and comprises a first substrate surface 32 with a first linear channel 34 and a second linear channel 36 formed in the first substrate surface 32. The closure band 20 further comprises a second substrate surface 42, opposite the first substrate surface 32, with a first linear ridge 44 and a second linear ridge 46 in a raised configuration from the second substrate surface 42. With additional reference to FIG. 4, the process of securing the closure band 20 about the hand 22 includes the steps of: (i) overlapping a second end section 48 of the closure band 20 over a first end section 38 of the closure band 20; (ii) inserting a portion of the first linear ridge 44 into a portion of the first linear channel 34; and (iii) inserting a portion of the second linear ridge 46 into a portion of the second linear channel 36 to completely secure the closure band 20. The closure band 20 may be trimmed to a desired length by the user, to terminate at a band end 30.

Figure 5:
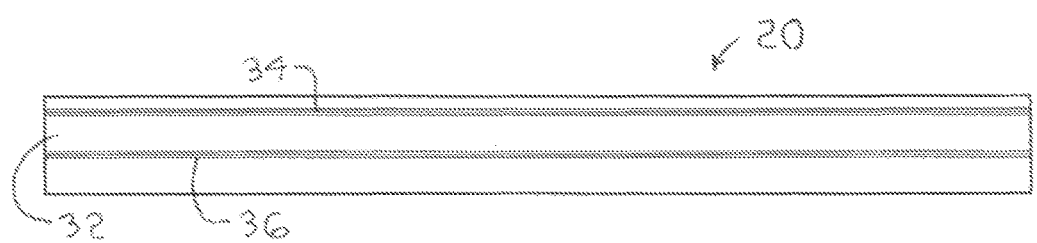
FIG. 5 is a view of one side of the closure band of FIG. 1 in a flat state.
Figure 6:
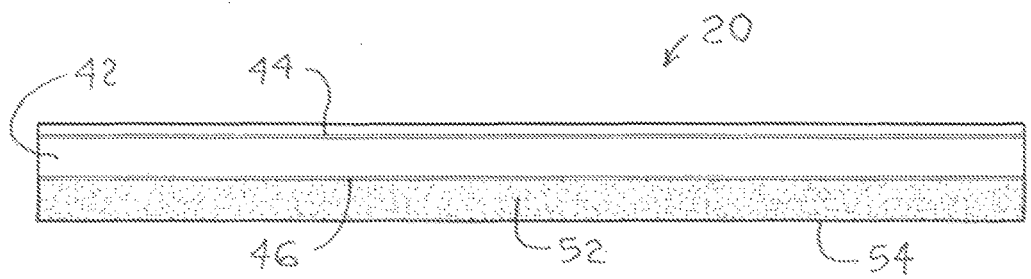
FIG. 6 is a view of another side of the closure band of FIG. 5.

FIG. 5 shows the first substrate surface 32 of the closure band 20. Note that the first linear channel 34 is substantially parallel to the second linear channel 36. FIG. 6 shows the second substrate surface 42 of the closure band 20. As shown, the first linear ridge 44 is substantially parallel to the second linear ridge 46. In an exemplary embodiment, there may be an adhesive strip 52 disposed on the second substrate surface 42 between an edge 54 and the second linear ridge 46. As noted above, the adhesive strip 52 functions to secure the closure band 20 to the user's hand 22. It should be understood that, in the various embodiments described herein, more or fewer adhesive strips can be used as the particular application may require.

Figure 7:
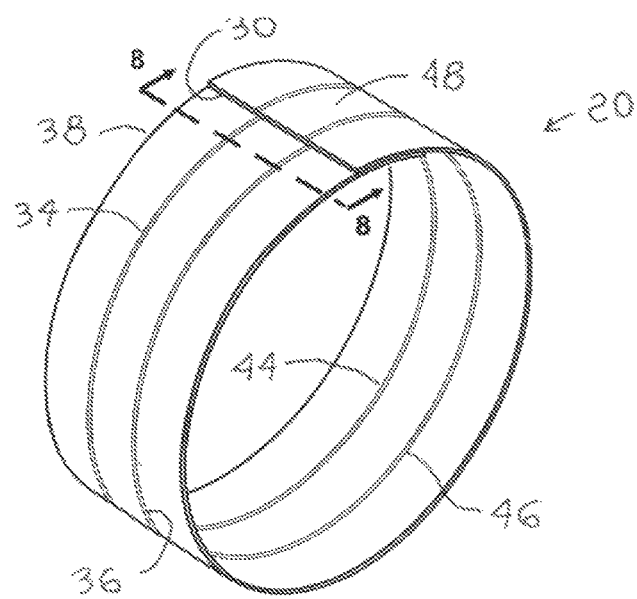
FIG. 7 is a view of the closure band of FIG. 1 in a closed state.

FIG. 7 is a perspective view of the closure band 20 in a looped configuration, similar to the state of the closure band 20 shown in FIG. 1. It can be seen that, in the configuration shown, the first linear ridge 44 and the second linear ridge 46 are disposed on the inside of the looped closure band 20, and the first linear channel 34 and the second linear channel 36 are disposed on the outside of the looped closure band 20. When secured to the user's hand 22, the first linear channel 34 and the second linear channel 36 face outward for attachment to a first cover ridge 24 and a second cover ridge 26, respectively, formed in the nonpermeable enclosure 12, shown in FIG. 2.

Figure 8:
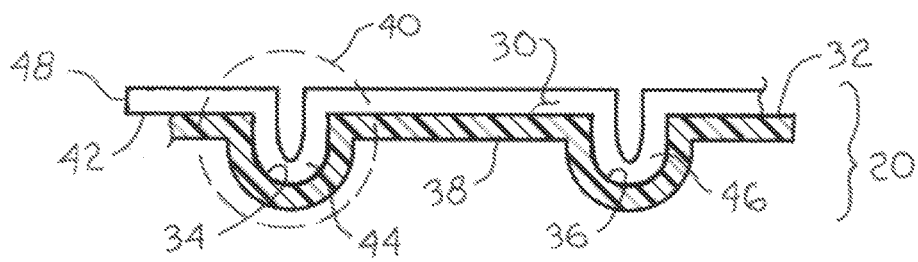
FIG. 8 is sectional view of the closure band of FIG. 7.

FIG. 8 is a cross sectional view of the closure band 20 viewed looking at the band end 30, as indicated by Section 8-8 arrows in FIG. 7. For clarity of illustration, the dimensions of the linear ridges 44, 46, the linear channels 34, 36, and the thickness of the closure band substrate have been exaggerated. The second end section 48 is placed onto the first end section 38 such that the second substrate surface 42 of the second end section 48 can be removably secured to the first substrate surface 32 of the first end section 38. When the first end section 38 is thus attached to the second end section 48, a closed band loop is formed configured for attachment to the user's wrist.

Figure 9:
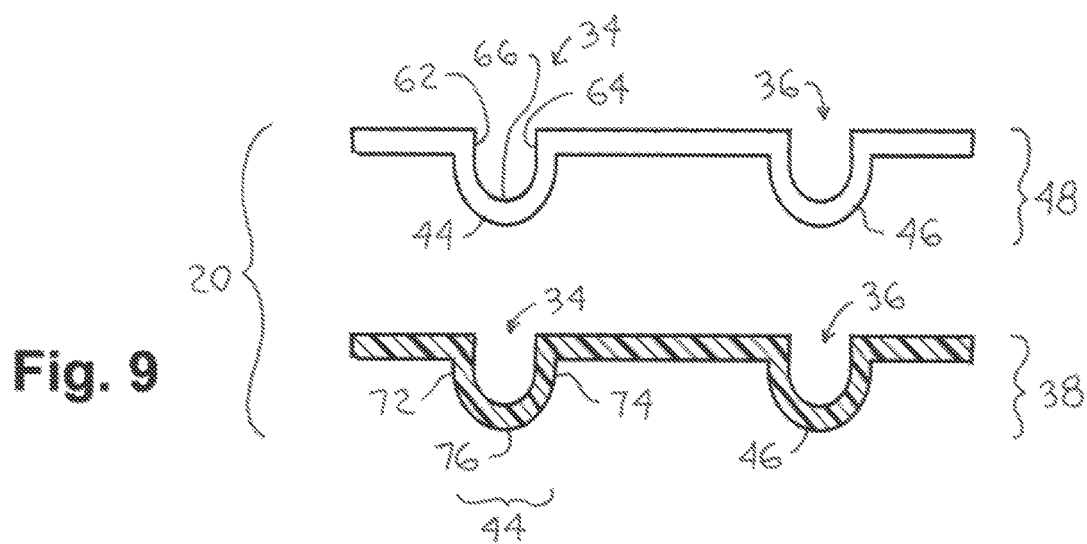
FIG. 9 is a sectional view of the closure band of FIG. 7 in an open state.

Referring to FIG. 9, the second end section 48 is shown in an unsecured position above the first end section 38, prior to the process of securing the closure band 20. The second end section 48 is positioned such that the first linear ridge 44 on the second end section 48 is positioned above the first linear ridge 44 on the first end section 38. Note that the first linear ridge 44 has an interior surface comprising a first substantially flat inner wall 62 joined to a second substantially flat inner wall 64 by a curved inner vertex 66. Note also that the first linear ridge 44 has an exterior surface comprising a first substantially flat outer wall 72 joined to a second substantially flat outer wall 74 by a curved outer vertex 76. It can be appreciated by one skilled in the relevant art that the linear channels 34, 36 extend into and lie substantially inside the linear ridges 44, 46 respectively. That is, the interior surfaces of the linear ridges are basically the linear channels, and each linear channel forms an inside surface of a respective linear ridge.

The curved inner vertex 66 and the curved outer vertex 76 function to allow the inner walls 62, 64 to slightly move apart from one another, or to slightly move towards one another, depending on external forces. Placement of the first linear ridge 44 into the first linear channel 34 causes the first linear ridge to compress slightly. This compression also causes the outer walls 72, 74 to bulge or move apart slightly. This results in a state of friction between the first linear ridge 44 and the first linear channel 34, for example, and serves to retain the first linear ridge 44 in the first linear channel 34. It can be appreciated by one skilled in the art that the first linear ridge 44 is merely the reverse side of the first linear channel 34. That is to say, if the linear ridges 44, 46 are formed on one surface of the closure band 20, corresponding linear channels 34, 36 are thereby formed in the reverse surface of the closure band 20.

When the closure band 20 is open and unsecured, the linear channels 34, 36 and the linear ridges 44, 46 appear as in FIG. 9. When the closure band 20 is secured, as shown in FIG. 8, the section of the first linear ridge 44 in the second end section 48 is placed into the section of the first linear channel 34 in the first end section 38, an action which slightly reduces the outer dimension of the section of the first linear ridge 44 in the second end section 48. This action also slightly increases the outer width of the first linear ridge 44 in the first end section 38. The section of the second linear ridge 46 in the second end section 48 is similarly inserted into the section of the second linear channel 36 in the first end section 38.

It can be appreciated by one skilled in the art that the insertion of the first linear ridge 44 into the first linear channel 34 functions to create a barrier 40 against moisture and contaminants at the attachment of the second end section 48 to the first end section 38. The insertion of the second linear ridge 46 into the second linear channel 36 similarly functions to create a moisture and contaminant barrier. In addition, the entire circumferential lengths of the cover ridges 24, 26 of the nonpermeable enclosure 12 are inserted into the entire circumferential lengths of the upper linear channels 34, 36 shown in FIG. 8. This engagement action creates a moisture and contaminant barrier along the entire interface of the protective covering 10 and the nonpermeable enclosure 12 to effectively seal off the user's hand 22 from moisture and contaminants, and allows the user to insert the covered hand 22 into water or other fluids without concern for wetting the wound 28.

Figure 10:
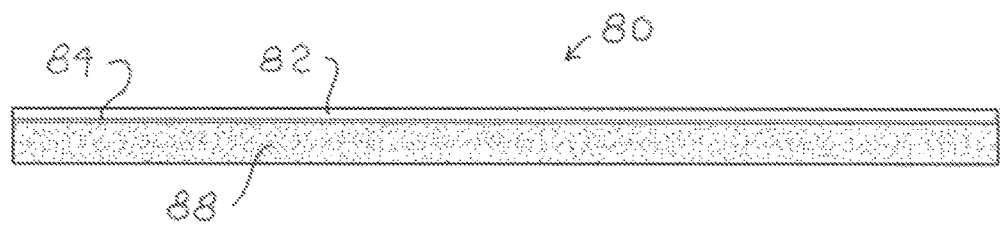
FIG. 10 is a view of a closure band having a single adhesive strip, in accordance with the present invention.
Figure 11:
FIG. 11 is a view of the back of the closure band of FIG. 10.

In an alternative embodiment, shown in FIGS. 10 and 11, a closure band 80 comprises a substantially linear substrate strip 82 with a linear ridge 84 on one side, and a corresponding substantially linear channel 86 on the reverse side of the substrate strip 82. An adhesive strip 88 may be provided adjacent the linear ridge 84.

Figure 12:
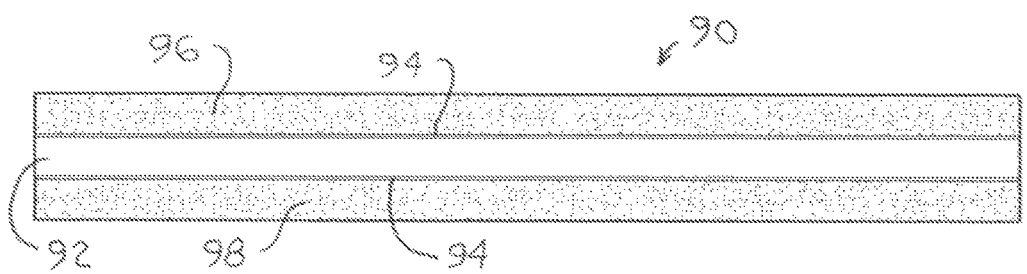
FIG. 12 is a view of a closure band having two adhesive strips, in accordance with the present invention.

In yet another embodiment, shown in FIG. 12, a closure band 90 comprises a substantially linear substrate strip 92, a pair of substantially parallel linear ridges 94 formed on the substrate strip 92, a first adhesive strip 96 disposed between one of the linear ridges 94 and one side of the linear substrate strip 92, and a second adhesive strip 98 disposed between the other of the linear ridges 94 and another side of the linear substrate strip 92. The closure band 90 can be used where a greater amount of adhesive is desired to keep the closure band 90 attached to and in place on the user's hand 22.

Figure 13:
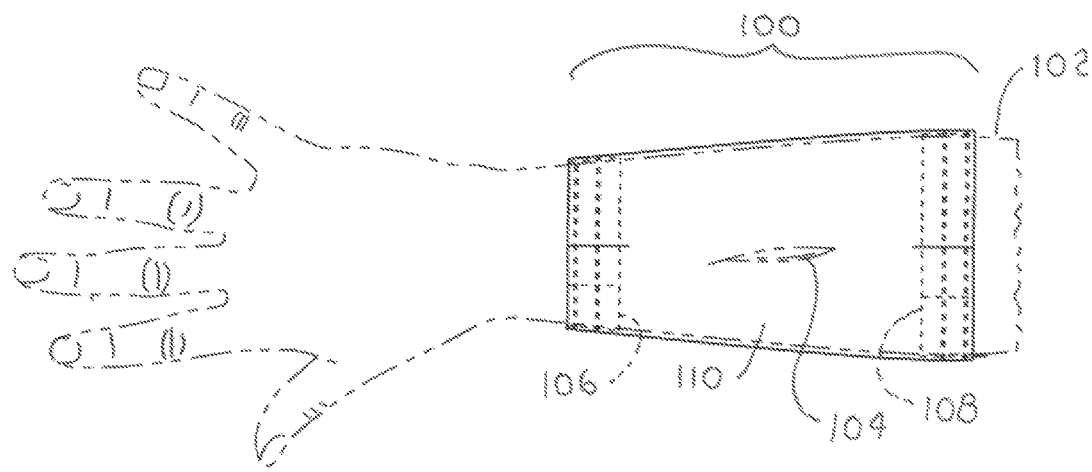
FIG. 13 is a view of a protective sleeve used on the forearm, in accordance with the present invention.
Figure 14:
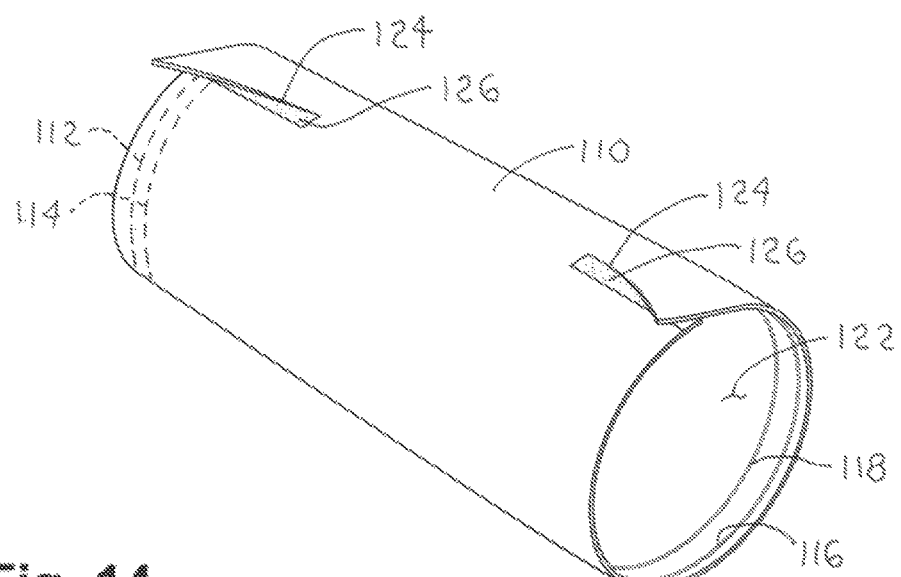
FIG. 14 is a view of the protective sleeve of FIG. 13.

FIG. 13 is an illustration of a protective sleeve 100 used on a selected region of the user's body, such as the forearm 102 of the user, to provide protection against contamination of a wound 104, for example. The protective sleeve 100 comprises a substantially cylindrical nonpermeable enclosure 110, a first closure band 106 near the user's wrist, and a second closure band 108 near the user's elbow. As shown in FIG. 14, the cylindrical nonpermeable enclosure 110 includes a first cover ridge 112 and a second cover ridge 114 configured to fasten to the first closure band 106, and a third cover ridge 116 and a fourth cover ridge 118 configured to fasten to the second closure band 108, similar to the fastening configuration of the protective covering 10 with the closure band 20 shown in FIG. 1.

FIG. 14 shows more explicitly that the cover ridges 112, 114 are disposed on an inner cylindrical surface 122 of the cylindrical nonpermeable enclosure 110. Adjustment slits 124, and corresponding adhesive strips 126, are provided at both ends of the cylindrical nonpermeable enclosure 110 so as to provide adjustment on the user's forearm and insure a water-tight fit. As shown in FIG. 13, the cylindrical nonpermeable enclosure 110 may have a slight taper so as to more closely conform to the shape of the user's forearm 102.

Figure 15:
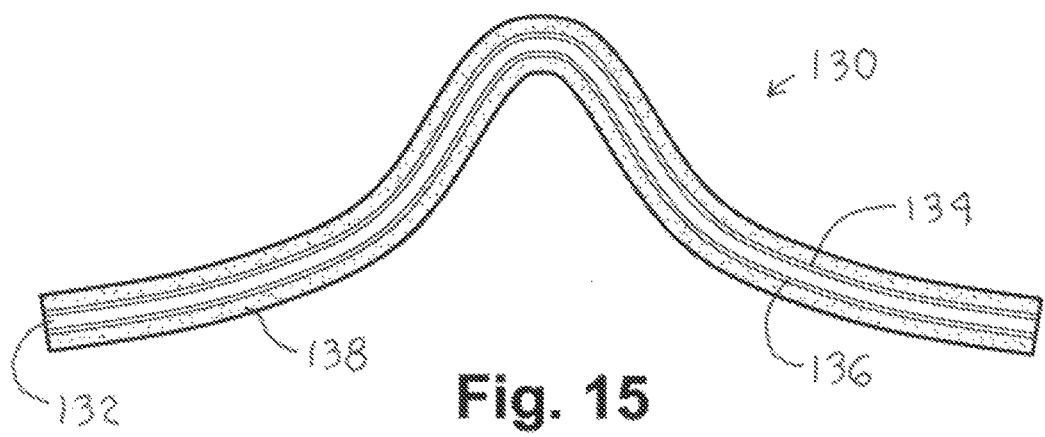
FIG. 15 is a view of a curved closure band with two adhesive strips, in accordance with the present invention.
Figure 16:
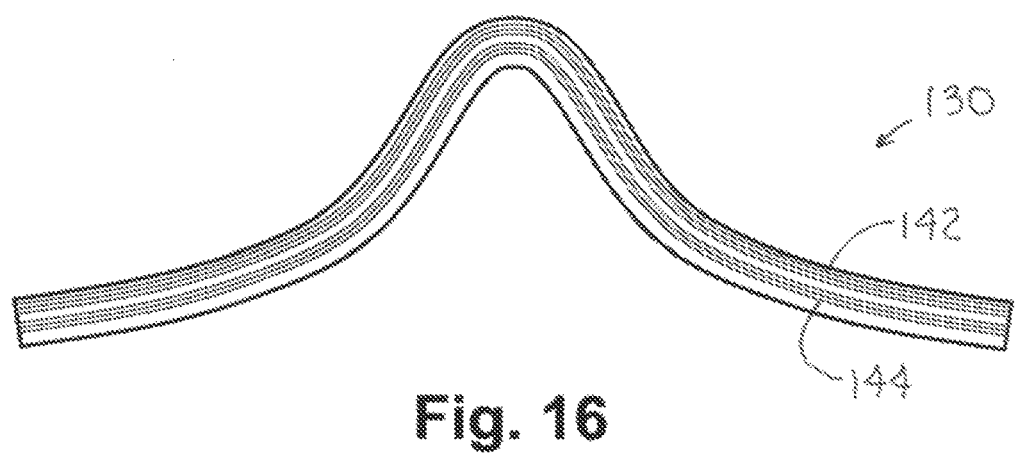
FIG. 16 is a view of the back surface of the curved closure band of FIG. 15.

FIG. 15 show an exemplary embodiment of a curved closure band 130 configured for use where the straight closure bands 20, 80, and 90 might cause occlusion of blood flow in the user's hand 22. The curved closure band 130 comprises a first curved ridge 134 and a second curved ridge 136 on a first surface of a substrate 132, with two adhesive strips 138 disposed between the curved ridges 134, 136 and adjacent edges of the substrate 132. Corresponding curved channels 142 and 144 are shown on the reverse side of the substrate 132, in FIG. 16.

Figure 17:
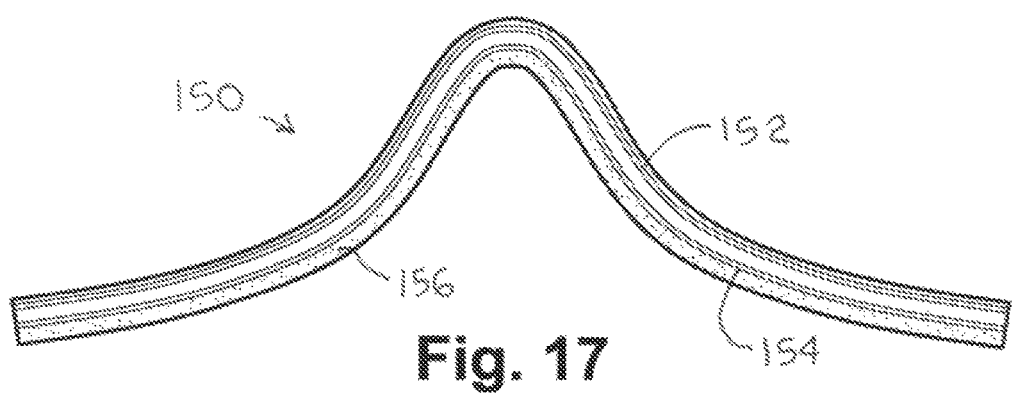
FIG. 17 is a view of a curved closure band with one adhesive strip, in accordance with the present invention.
Figure 18:
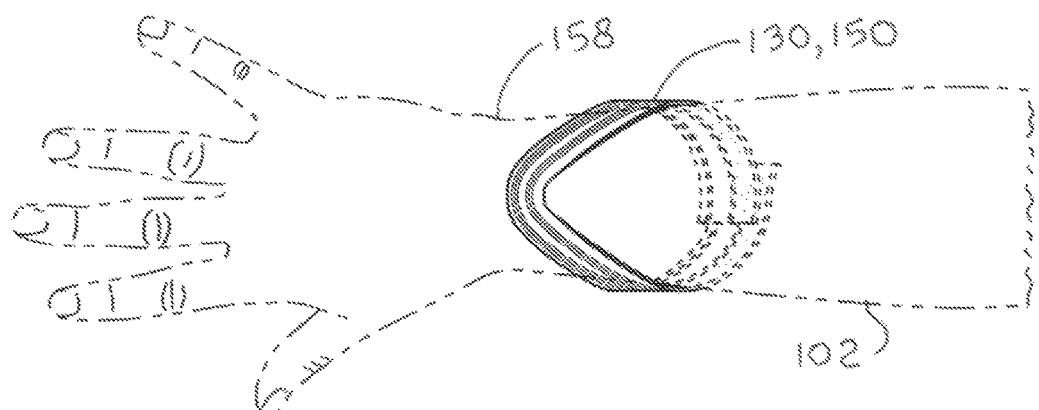
FIG. 18 is a view of the front of the curved closure band of FIG. 15 as worn on the hand.
Figure 19:
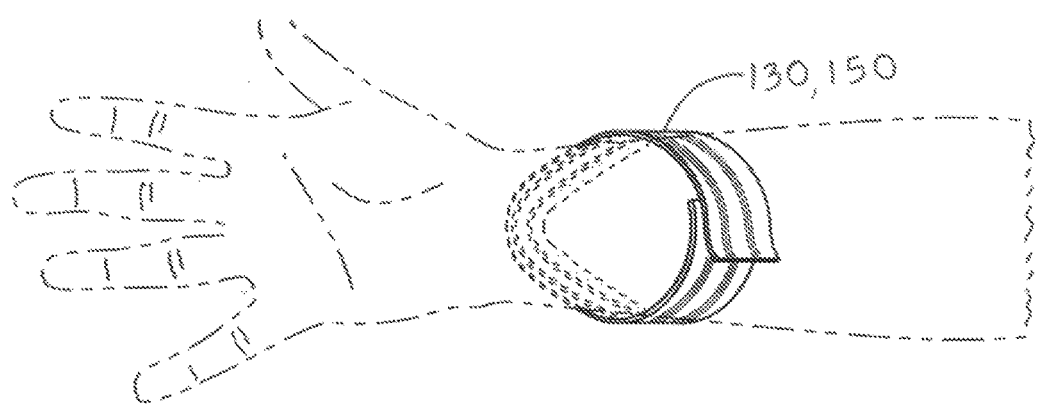
FIG. 19 is a view of the back of the curved closure band of FIG. 15.
Figure 20:
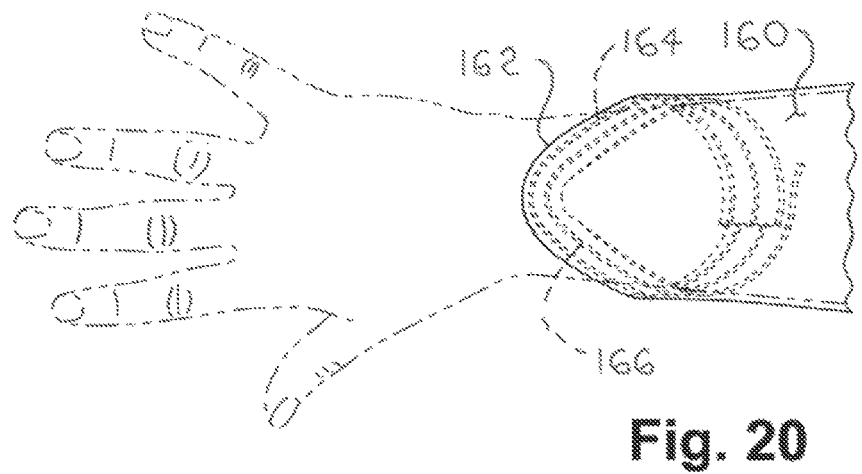
FIG. 20 is a view of the curved closure band of FIG. 15 with an attached extended sleeve.

In an alternative embodiment, shown in FIG. 17, a curved closure band 150 includes a first curved ridge 152 and a second curved ridge 154 on the substrate 132. The curved closure band 150 includes a single adhesive strip 156. FIGS. 18 and 19 illustrate the manner in which the curved closure bands 130 and 150 may be secured on the user's arm 22. An extended sleeve 160 has a curved sleeve end 162 shaped to conform to the curved closure bands 130 and 150, as shown in FIG. 20. The extended sleeve 160 includes a first curved ridge 164 and a second curved ridge 166 conforming to the sizes and shapes of the curved ridges 134, 136, shown in FIG. 15, and of the curved ridges 152, 154, shown in FIG. 17. Attachment of the extended sleeve 160 to the curved closure bands 130 and 150 includes the insertion of the curved ridges 164, 166 into the corresponding curved channels 142, 144, a method similar to the attachment method of securing the protective covering 10 to the closure band 20 as described above.

Figure 21:
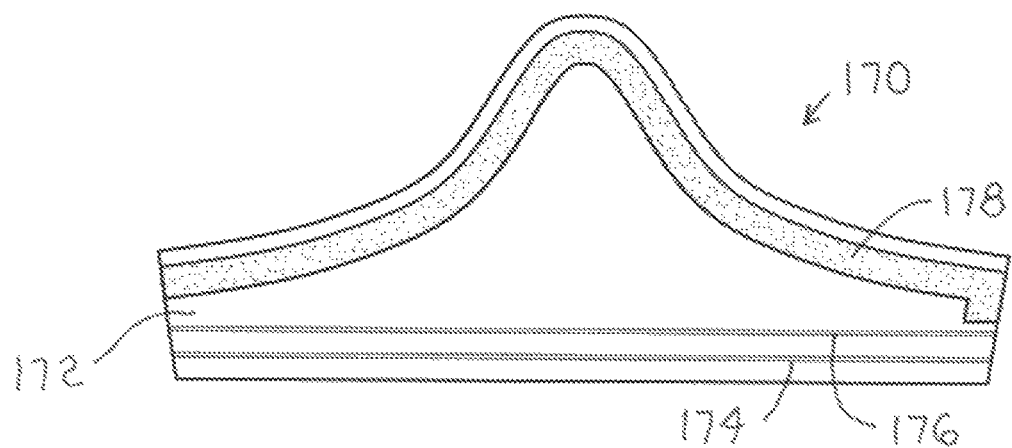
FIG. 21 is a front view of a closure cuff with one adhesive strip and two linear ridges, in accordance with the present invention.
Figure 22:
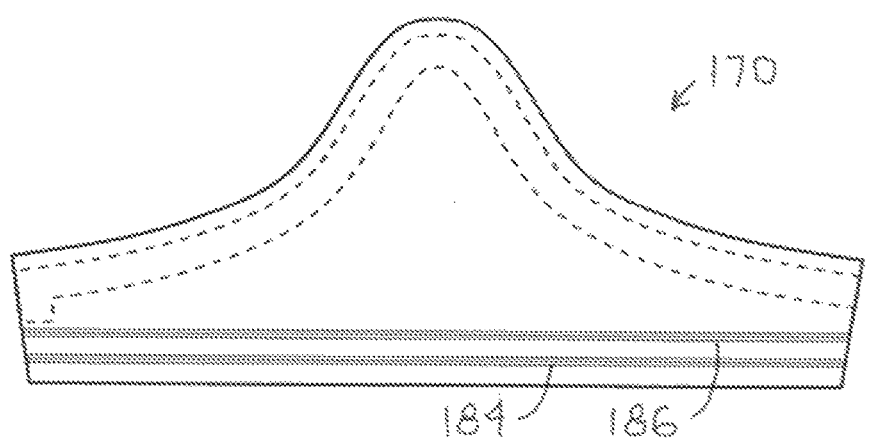
FIG. 22 is a rear view of the closure cuff of FIG. 21 showing two linear channels.

FIG. 21 shows a closure cuff 170 that can be used on the user's wrist 158 to secure a conforming protective covering over the user's forearm 102. The closure cuff 170 comprises a substrate 172 having a crested shape, a first linear ridge 174 and a second linear ridge 176 at the base of the substrate 172, and a strip of adhesive 178 along the curved border of the substrate 172. FIG. 22 shows the linear channels 184, 186 formed with the corresponding linear ridges 174, 176 at the base of the substrate 172.

Figure 23:
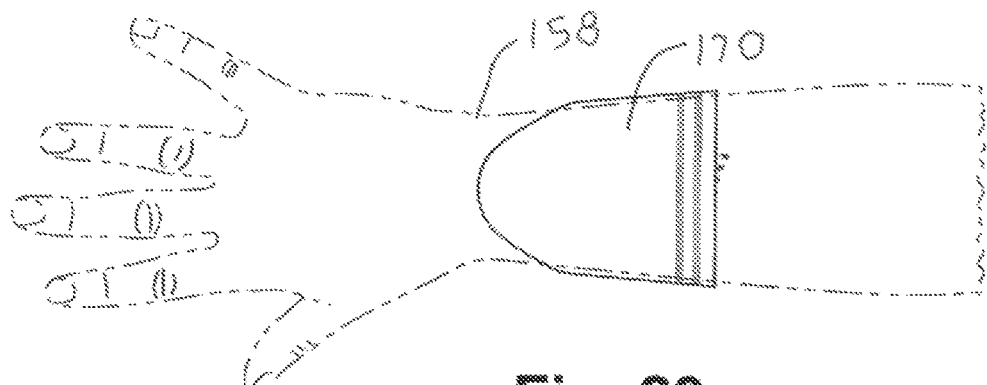
FIG. 23 is a view of the front of the closure cuff of FIG. 21 as worn on the hand.
Figure 24:
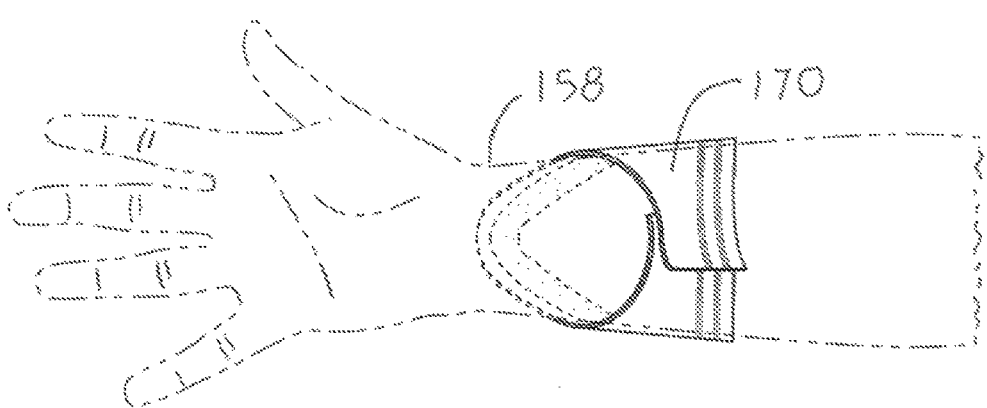
FIG. 24 is a view of the back of the closure cuff of FIG. 23.
Figure 25:
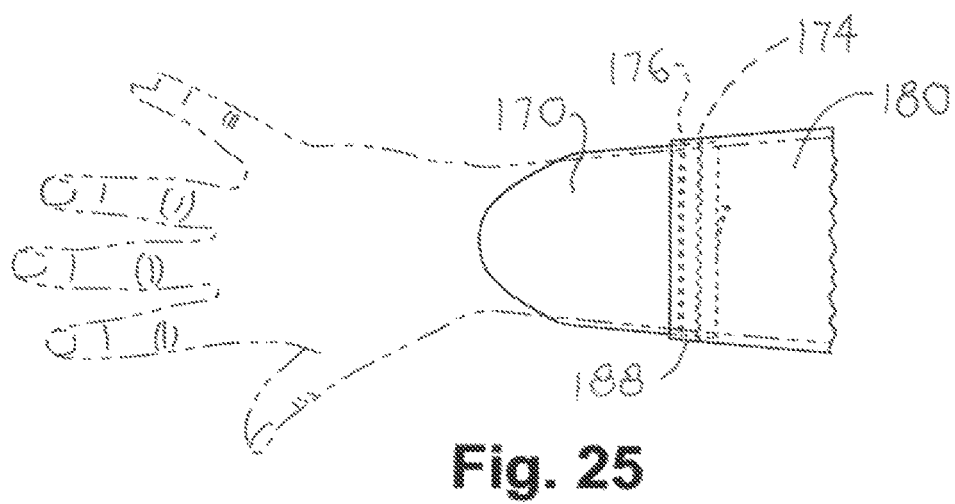
FIG. 25 is a view of the closure cuff of FIG. 23 with an attached extended sleeve.

FIGS. 23 and 24 show the closure cuff 170 as may be worn on the user's wrist 158. When in place, a protective sleeve 180 may be attached to the closure cuff 170 by inserting sleeve ridges 188 into the linear channels 174, 176 of the closure cuff 170, in FIG. 25, similar to the method used for securing the protective covering 10 to the closure band 20 as described above.

Figure 26:
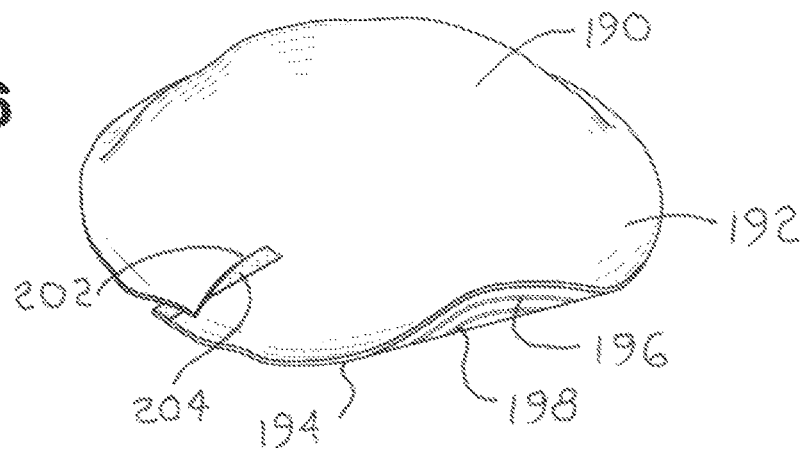
FIG. 26 is a view of a protective pouch covering, in accordance with the present invention.

Shown in FIG. 26 is a protective pouch covering 190 adapted for use over a flat area of a user's body, such as the chest region. The protective pouch covering 190 comprises a nonpermeable enclosure pouch 192 generally shaped as a shallow pouch, and fabricated from a plastic material, a coated fabric, or other suitable flexible material, for example. The nonpermeable enclosure pouch 192 includes an annular lip 194 serving as the perimeter of the shallow pouch, where the annular lip 194 has a first cover ridge 196 and a second cover ridge 198 formed in the annular lip 194. It should be understood that the annular lip 195 is shaped as a closed curve, and need not be circular. Hence, the cover ridges 196, 198 are not necessarily circular in shape. A slit 202 and an adjacent strip of adhesive 204 are provided in the nonpermeable enclosure pouch 192 to allow for adjustment in the dimensions of the protective pouch covering 190, as may be required.

Figure 27:
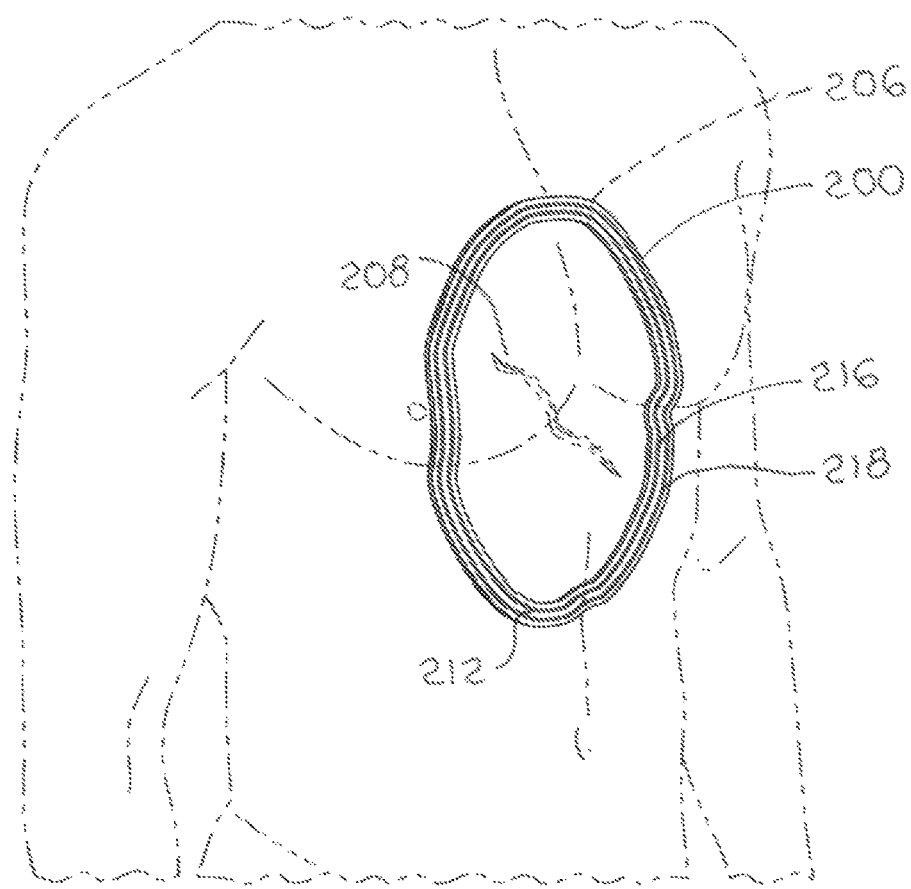
FIG. 27 is a view of a circumferential band placed over a wound on the chest of a patient, in accordance with the present invention.

As shown in FIG. 27, a circumferential band 200 has been placed so as to enclose a selected region of the user's body. In the example shown, the circumferential band comprises a closed loop that has been placed about a wound 208 on the chest of a patient. The configuration of the circumferential band 200 may be similar to the configuration of the linear band 90, shown in FIG. 12 above. That is, the circumferential band 200 may comprise a circumferential substrate 212 having a first circumferential channel 216 and a second circumferential channel 218 formed in the circumferential substrate 212. At least one circumferential strip of adhesive 206 may be provided on the reverse side of the circumferential substrate 212 to enable a user to secure the circumferential band 200 to the chest of the patient, or to another selected region of the user's body.

Figure 28:
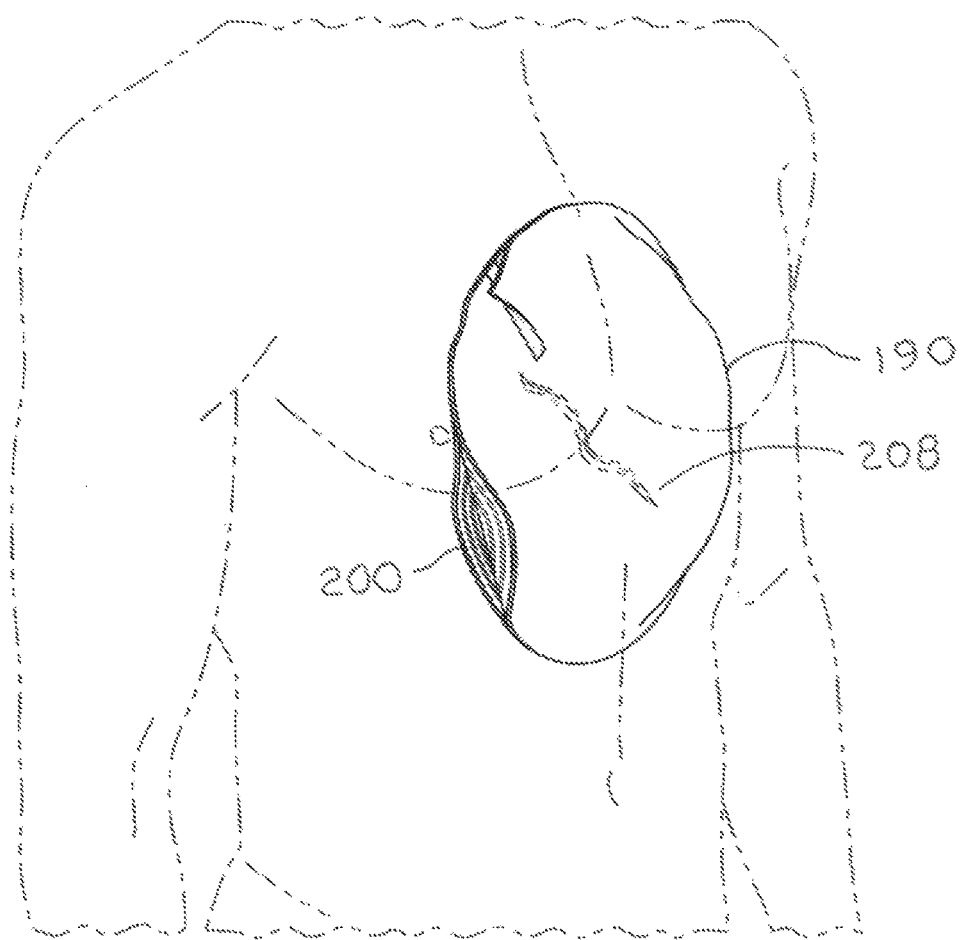
FIG. 28 is a view of the protective pouch covering of FIG. 26 secured to the circumferential band of FIG. 27.

FIG. 28 illustrates a method of attaching the protective pouch covering 190 to the circumferential band 200 by inserting the cover ridges 196, 198 into the respective circumferential channels 216, 218. It can be appreciated by one skilled in the relevant art that the disclosed system of providing a protective covering for the wound 208 allows for replacement of the protective pouch covering 190 as desired, without the need to also replace the circumferential band 200.

It is to be understood that the description herein is only exemplary of the invention, and is intended to provide an overview for the understanding of the nature and character of the disclosed devices and methods for providing protection from ambient moisture and contaminants. The accompanying drawings are included to provide a further understanding of various features and embodiments of the method and devices of the invention which, together with their description serve to explain the principles and operation of the invention.

What is claimed is:

1. A protective device suitable for keeping moisture from a selected region of a body, said protective device comprising:
   a linear closure band formed from a flexible substrate, said linear closure band having a first channel imbedded in a first substrate surface and a first ridge disposed on a second substrate surface in a raised configuration, said linear closure band further having an adhesive strip on said second substrate surface for attaching said linear closure band to the body proximate the selected region; and
   a nonpermeable enclosure formed from a clear, waterproof fabric, said nonpermeable enclosure having a first cover ridge disposed on a surface of said nonpermeable enclosure in a raised configuration, said first cover ridge inserted into said first channel so as to produce a barrier against moisture and contaminants between said linear closure band and said nonpermeable enclosure.

2. The protective device of claim 1 further comprising a second channel in said linear closure band and a second cover ridge in said nonpermeable enclosure, said second cover ridge disposed so as to allow releasable attachment to said second channel when said first cover ridge is releasably attached to said first channel.

3. The protective device of claim 1 wherein said first channel forms an inside surface of said first ridge.

4. The protective device of claim 1 wherein said linear closure band is formed into a closed loop for enclosing the selected region.

5. The protective device of claim 1 wherein said linear closure band comprises a first end section and a second end section, said first end section attached to said second end section so as to form a closed band for attachment to a user's wrist.

6. The protective device of claim 1 wherein said linear closure band further comprises a crested shape to form a closure cuff such that said first channel has a linear shape, and said adhesive strip has a curved shape.

7. A protective device suitable for keeping moisture from a selected region of a body, said protective device comprising:
   a linear closure band formed from a flexible plastic substrate, said linear closure band having a first channel and a second channel imbedded in a first substrate surface and a first ridge and a second ridge disposed on a second substrate surface in a raised configuration, said linear closure band further having a pair of adhesive strips on said second substrate surface for attaching said linear closure band to the body proximate the selected region; and
   a nonpermeable enclosure formed from a clear, hypoallergenic material, said protective covering having a first cover ridge and a second cover ridge disposed on a surface of said protective covering in a raised configuration, said first cover ridge inserted into said first channel so as to produce a barrier against moisture and contaminants between said linear closure band and said protective covering, and said second cover ridge inserted into said second channel so as to produce a second barrier.

8. The protective device of claim 7 wherein said linear closure band is formed into a closed loop for enclosing the selected region.

9. The protective device of claim 7 wherein said linear closure band is configured to enclose a wearer's wrist.

10. The protective device of claim 7 wherein said pair of adhesive strips are positioned for placement onto a wearer's wrist.

11. The protective device of claim 7 wherein said linear closure band is configured to enclose a wearer's forearm.

12. The protective device of claim 7 wherein said pair of adhesive strips are positioned for placement onto a wearer's forearm.

13. The protective device of claim 7 wherein said pair of adhesive strips are positioned for placement against both a wearer's forearm and said wearer's wrist.

14. The protective device of claim 7 wherein said first channel forms an inside surface of said first ridge and said second channel forms an inside surface of said second ridge.

15. A method for keeping moisture from a selected region of a body, said method comprising the steps of:

providing a closure band formed from a flexible substrate, said closure band having a channel imbedded in a first substrate surface and a ridge disposed on a second substrate surface in a raised configuration, said channel extending into said ridge, said closure band further having an adhesive strip on said second substrate surface;

attaching said closure band to the selected region of the body using said adhesive strip;

providing a nonpermeable enclosure configured to cover the selected region of the body, said nonpermeable enclosure having a cover ridge configured for releasable attachment to said channel; and inserting said cover ridge into said channel so as to produce a barrier against moisture and contaminants.

16. The method of claim 15 wherein said closure band comprises a closed loop.

* * * * *